United States Patent [19]

Woodard et al.

[11] Patent Number: 5,329,000
[45] Date of Patent: Jul. 12, 1994

[54] PURIFICATION OF DNA WITH SILICON TETRAHYDRAZIDE

[75] Inventors: Daniel L. Woodard, Raleigh; Adriann J. Howard, Durham, both of N.C.

[73] Assignee: Becton, Dickinson and Company, Franklin Lakes, N.J.

[21] Appl. No.: 785,837

[22] Filed: Oct. 31, 1991

[51] Int. Cl.$^5$ .................. C07H 1/06; C07H 21/00; C07H 21/02; C07H 21/04
[52] U.S. Cl. .................. 536/25.4; 435/6; 435/274; 935/19; 935/20
[58] Field of Search ............ 935/19; 436/6; 536/27, 536/24, 33, 25.4; 435/274

[56] References Cited

U.S. PATENT DOCUMENTS

| | | | |
|---|---|---|---|
| 4,833,239 | 5/1989 | DeBonville et al. | 536/27 |
| 4,900,677 | 2/1990 | Hewitt | 435/259 |
| 4,921,952 | 5/1990 | Longmire et al. | 536/27 |
| 5,106,966 | 4/1992 | Tilzer et al. | 536/27 |

OTHER PUBLICATIONS

Sek C. Chow et al., *Analytical Biochemistry* 183:42 (1989).
Randy M. McCormick, *Analytical Biochemistry* 181:66 (1989).
M. A. Marko, et al., *Analytical Biochemistry* 121:382 (1982).
Louise H. Lutze et al., *Nucleic Acids Research* 18:6150 (1990).
R. Boom et al., *Journal of Clin. Microbiology* 28:495 (1990).
Bert Vogelsteil et al., *Proc. Natl. Acad. Sci.* 76:615 (1979).
Erik H. Willis et al., *BioTechniques* 9:92 (1990).

*Primary Examiner*—Johnnie R. Brown
*Assistant Examiner*—Gary L. Kunz
*Attorney, Agent, or Firm*—Donna R. Fugit

[57] ABSTRACT

A process for purifying DNA in which the DNA is bound to silicon tetrahydrazide in the presence of less than 2M chaotrope, low salt buffers, or water. The DNA is then eluted with low salt buffer or by heating in water.

6 Claims, No Drawings

PURIFICATION OF DNA WITH SILICON TETRAHYDRAZIDE

FIELD OF THE INVENTION

The invention is in the field of molecular biology. In particular, the invention is in the area of deoxyribonucleic acid purification.

BACKGROUND OF THE INVENTION

The continued advances in molecular biology and related disciplines present continued needs for improvements in tools associated with fully appreciating and developing the advanced technology.

A wide range of technologies involve the use of deoxyribonucleic acids (DNA) in a variety of forms. For example, advances in the area of recombinant DNA technology continually require the use of DNA in the form of probes, genomic DNA, and plasmid DNA.

Advances in the area of diagnostics also continue to utilize DNA in a variety of ways. For example, DNA probes are routinely used in the detection and diagnosis of human pathogens. Likewise, DNA is used in the detection of genetic disorders. DNA is also used in the detection of food contaminants. And, DNA is routinely used in locating, identifying and isolating DNA of interest for a variety of reasons ranging from genetic mapping to cloning and recombinant expression.

In many instances DNA is available in extremely small amounts, and isolation and purification procedures can be laborious and time consuming. The often time consuming and laborious procedures can lead to loss of DNA. In the purification of DNA from specimens obtained from serum, urine, and bacterial cultures, there is the added risk of contamination and false-positive results.

Typical DNA purification protocols involve the use of caustic and poisonous compositions. The typical DNA purification protocol uses high concentrations of chaotropic salts such as sodium iodine and sodium perchlorate.

There are numerous protocols for purifying DNA. As evidenced by recent activity in the area of DNA purification, there is a continued pursuit for optimal DNA purification protocols. U.S. Pat. No. 4,923,978 discloses a process for purifying DNA in which a solution of protein and DNA is passed over a hydroxylated support and the protein is bound and the DNA is eluted. U.S. Pat. No. 4,935,342 discloses purification of DNA by selective binding of DNA to anion exchangers and subsequent elution. U.S. Pat. No. 4,946,952 discloses DNA isolation by precipitation with water-soluble ketones. A DNA purification procedure using chaotropes and dialyzed DNA is disclosed in U.S. Pat. No. 4,900,677.

While the present protocols for purifying DNA are able to accomplish their goal, it is desirable to purify DNA without the use of such caustic and poisonous compounds such as the most often used chaotropes in addition to obtaining increased amounts of DNA.

SUMMARY OF THE INVENTION

The invention provides the monomer unit composition:

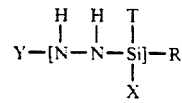

wherein T is HN—NH$_2$ or Si(OH)$_3$, Y is H, R is HN—NH$_2$, and X is HN—NH$_2$, and repeating units of the composition comprising the formula:

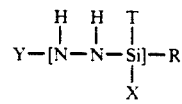

wherein T is HN—NH$_2$ or Si(OH)$_3$, Y is H or a monomer unit, R is HN—NH$_2$ or a monomer unit, X is HN—NH$_2$ or a monomer unit, and compositions comprising the above monomer and repeating units thereof. Repeating units described above can include from about 2 up to infinity. Ranges include 2 to 100,000,000, and 2 to 100,000.

The invention can be used to purify DNA from a variety of sources and from a variety of forms. The process uses the composition of the invention and renders the use of binding buffers, such as chaotropes, optional. The DNA can be bound in an aqueous solution such as TE buffer at room temperature. In addition, the DNA can be eluted into water from the compositions of the invention by heating, or generally used elution buffers such as TE or 1X TAE can be employed. Sources of DNA for purification include bacteria, bacteriophage, specimens, plants, animals, and the like. DNA can be found in a variety of forms and includes single-stranded, double-stranded, circular, and linear. The invention can be practiced with DNA from any source in any form.

DETAILED DESCRIPTION

The invention provides the monomer unit composition:

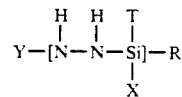

wherein T is HN—NH$_2$ or Si(OH)$_3$, Y is H, R is HN—NH$_2$, and X is HN—NH$_2$, and repeating units of the composition comprising the formula:

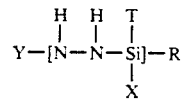

wherein T is HN—NH$_2$ or Si(OH)$_3$, Y is H or a monomer unit, R is HN—NH$_2$ or a monomer unit, X is HN—NH$_2$ or a monomer unit, and compositions comprising the above monomer and repeating units thereof. Repeating units described above can include from about 2 up to infinity. Ranges include 2 to 100,000,000, and 2 to 100,000.

The surface provides for bonding of DNA while also allowing easy recovery of DNA from the surface.

Also provided is a process for purifying DNA which comprises contacting DNA with a composition of the formula:

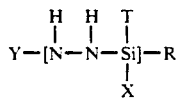

wherein T is HN—NH$_2$ or Si(OH)$_3$, Y is H, R is HN—NH$_2$, and X is HN—NH$_2$, and repeating units of the composition comprising the formula:

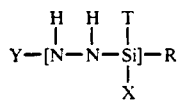

wherein T is HN—NH$_2$ or Si(OH)$_3$, Y is H or a monomer unit, R is HN—NH$_2$ or a monomer unit, X is HN—NH$_2$ or a monomer unit, and compositions comprising the above monomer and repeating units thereof.

Reaction products of H$_2$NNH$_2$ and SiCl$_4$ are also provided.

The invention also provides a method for making the composition of the formula:

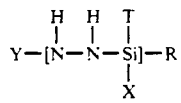

wherein T is HN—NH$_2$ or Si(OH)$_3$, Y is H, R is HN—NH$_2$, and X is HN—NH$_2$, and repeating units of the composition comprising the formula:

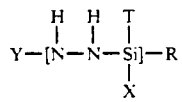

wherein T is HN—NH$_2$ or Si(OH)$_3$, Y is H or a monomer unit, R is HN—NH$_2$ or a monomer unit, X is HN—NH$_2$ or a monomer unit. Repeating units described above can include from about 2 up to infinity. Ranges include 2 to 100,000,000, and 2 to 100,000.

Generally, reaction products of H$_2$NNH$_2$ and SiCl$_4$ result in a bead like structure comprising repeating units of the above referenced monomer unit.

It is possible that the electronic nature of this polymer is such that surface modifications can be made that are of a more conventional nature but are changed electronically due to the presence of this polymer being at the center of the bead (making it a more efficient surface for the purposes described in this disclosure). For example, the surface could be modified with SiCl$_4$ followed by hydration which would result in a silanol coating on the surface. Other modifications could involve use of NaOH resulting in a more polarized surface. The exposure of the repeating unit is what interacts with the DNA, and thus surfaces comprising the repeating unit are also suitable for practicing the invention. Surfaces which can be designed to comprise compositions of the invention include dipstick configurations, tubes, vials, filtration devices, and the like.

The procedure for obtaining the compositions of the invention generally comprises diluting H$_2$NNH$_2$ with tetrahydrofuran (THF), followed by cooling. SiCl$_4$ is then added until hydrogen chloride gas HCl(g) no longer elutes, then excess H$_2$NNH$_2$ is added to ensure complete reaction of SiCl$_4$.

The invention also provides a process for purifying DNA which comprises contacting DNA with compositions of the invention.

The process for producing the compositions of the invention and the reaction products of (hydrazine) H$_2$NNH$_2$+SiCl$_4$ comprises the addition of hydrazine to tetrahydrofuran, followed by cooling. Any solvent not reacting with the silicon tetrachloride can be used, not just THF. The reaction can also be performed without solvent. The ratio of hydrazine to tetrahydrofuran is generally about 1 part to 10 parts, preferably about 1 part to 5 parts. SiCl$_4$ is then added to the hydrazine mixture until production of HCl gas stops. The amount of SiCl$_4$ to hydrazine is generally about 10 to 1, preferably about 6 to 1. This solution is stirred for about thirty (30) minutes. Excess hydrazine is then added to this solution and stirred for about thirty (30) minutes. The amount of hydrazine added at this point is sufficient to ensure that all SiCl$_4$ has reacted. The resultant product is filtered then washed and dried. Suitable washing reagents include acetone and the like. The product is now ready for use in purifying DNA.

The start of any DNA purification or isolation procedure requires obtaining the desired DNA from its source. Typical protocols for obtaining DNA from specimens such as serum, urine and bacterial cultures are well known and routinely carried out. Likewise, the ability to obtain DNA from genomic libraries and the like are routine. The key to the invention is the ability to purify DNA, once obtained from its source. Typical procedures for obtaining DNA end with a suspension of the DNA in solution. References include those for isolation of DNA from biological samples, Harding, J. D., Gebeyehu, G., Bebee, R., Sims, D., Ktevan, L., *Nucleic Acids Research*, 17:6947 (1989), and Marko, M. A., Chipperfield, R., and Birnboim, H. C., *Analytical Biochemistry*, 121:382 (1982). Procedures for isolation of plasmid DNA can be found in Lutze, L. H., Winegar, R. A., Nucleic Acids Research 20:6150 (1990). Extraction of double-stranded DNA from biological samples can be found in Yamada, O., Matsumoto, T., Nakashima, M., Hagri, S., Kamahora, T., Ueyama, H., Kishi, Y., Uemura H., Kurimura, T., *Journal of Virological Methods* 27:203 (1990). Most DNA solutions comprise the DNA in a suitable buffer such as TE (Tris-EDTA), TEA (40 mm Tris-acetate, 1 mm EDTA) buffer, or a lysate.

Once the DNA is obtained in a suitable solution, a binding matrix is typically added to the solution. Generally used binding matrixes are silica in the form of glass or diatoms. However, procedures using silica require high concentrations of chaotropes or alcohols for the DNA to bind to the surfaces. Popular chaotropes include sodium iodide (NaI), urea, guanidinium Hydrochloride, sodium perchlorate (NaClO$_4$), and potassium bromide (KBr). Chaotropes and alcohols can be toxic, caustic, flamable and/or expensive. The process of the present invention does not require the presence of chaotropes or alcohols for binding to surfaces of the invention. Such processes would therefore bind DNA in an aqueous solution. However, if desired, chaotropes, alcohols and the like can be used with the process of the invention.

Typical procedures for using the process of the invention include the addition of the composition of the invention to a solution of DNA, which is generally followed by the addition of a binding buffer. At this point, it is advantageous that the process of the invention does not require a binding buffer. Room temperature is suitable for the process. The solution can be incubated for a brief period at room temperature. After spinning, the supernatant can be discarded and the pellet washed. The DNA can then be eluted.

When practicing the process of the invention, typically the composition of the invention is added to a container comprising DNA. Weight ranges in the range from about 1:10 to 1:1 composition weight:water can be used. Preferably excess amounts of water are avoided and buffers such as TE can be used in place of water.

Next, a binding buffer is added if used. After a brief incubation period at room temperature from about 1 to 20 minutes, preferably about 10, the container can be spun to obtain a pellet and supernatant fractions. The supernatant is separated and the pellet is washed with a reagent such as ethanol diluted with 50 mM Tris. A preferred wash reagent concentration is 80% ethanol. DNA can then be eluted from the compositions of the invention by using elution buffers such as TE buffer, 1X TAE buffer, and 1×TBE buffer. More importantly, the use of elution buffers can be eliminated altogether, and DNA eluted in water by heating. For maximum yields the elution step can be repeated.

The chemical compositions of the invention can be conveniently assembled into a kit. A kit comprising the composition of the invention can include the composition in a container, such as a vial, with a suitable buffer, such as TE buffer and TAE buffer and optionally include a container of a binding buffer such as chaotropes, a container of wash buffer, such as a solution of ethanol diluted with 50 mM tris or 1×TAE, and a container of elution buffer, such as TE buffer, 1×TAE buffer, and 1×TBE buffer. Such a kit would allow convenient purification of DNA.

The following examples illustrate the specific embodiments of the invention described in this document. As would be apparent to skilled artisans, various changes and modifications are possible and are contemplated within the scope of the invention described.

EXAMPLES

Example 1

Synthesis of Silicon Tetrahydrazide

Equation

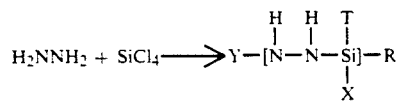

Materials

| Materials: | |
|---|---|
| THF | (Aldrich Lot #63314PM Milwaukee, WI) |
| H$_2$NNH$_2$ | (Aldrich Lot #01427KX Milwaukee, WI) |
| SiCl$_4$ | (Petrarch Systems Lot #80879 Bristol, PA) |

Procedure

4ml of H$_2$NNH$_2$ is added to 20 ml THF. Cool to 0° C. in an ice bath. 25 ml of SiCl$_4$ is added to an addition funnel and clamped above the erlenmeyer flask containing the hydrazine. Slowly add the SiCl$_4$ until HCl gas stops eluting. Add 0.5 ml SiCl$_4$ and stir for about 30 minutes. Add about 3 ml hydrazine, stir for about 30 minutes, filter, wash with 500 ml acetone, air dry about 1 hour, oven dry about 1 hour. Store in a desicator.

EXAMPLE 2

This experiment describes how the DNA binding capacity of SUPER FINE SUPER FLOSS CELITE (the industry standard (Manville)) was determined and what that capacity is. It was determined that SUPER FINE SUPER FLOSS CELITE strongly binds and elutes DNA at 2.5M with NaClO$_4$ as the binding buffer.

Materials

Super Fine Super Floss (SFSF) (Sample from Manville, Denver, Colo. (1:5 w/w in H$_2$O))
λDNA (BRL Cat. 56125A, Lot AJU702)
50 mM Tris pH 7.0 (Dilute from 1M stock) BRL Cat. 5505UA, Lot 60926
(PREP-A-GENE KIT (Bio-Rad, Richmond, Calif.))
Binding Buffers (Diluted from 6M stock) NaClO$_4$ Fisher Cat. 5490-500, Lot 914199
Wash Buffer 80% Ethanol in 50 mM Tris, pH 7.0
Elution Buffer Milli Q H$_2$O
Ethidium Bromide (10mg/ml) Sigma Cat. E-8751, Lot 99F3722
1% agarose BRL Cat. 5510UA, Lot 9N2204
1X TAE (from 50X stock) Tris Base-Sigma CAT T-1503, Lot 80H5633 Acetic Acid—Fisher A38-500 EDTA—Sigma CAT ED255, Lot 117F-0026
Type II Loading Dye (25% Ficoll 400, 0.25% Bromophenol Blue, 0.25% xylene cyanol Ficoll 400 - Sigma CAT F4375, Bromophenol
Blue - BIO-RAD CAT 161-0404, Lot M 1264, Xylene Cyanole—Sigma CAT X-4126, Lot 8043740)
Type 57 and 55 POLAROID Film Methods 1. Two groups of reactions are set up, one for each surface type. Each surface has 8 tubes containing 50μl of the DNA solution. This solution is 0.5μl λDNA in 50μl 50 mM Tris, pH 7.0 for 31μg DNA/reaction. The titration ranges from 0M NaClO$_4$ to 6M NaClO$^4$.
2. Add 20μl of each surface to the reaction mixes.
3. Add 400μl Binding Buffer according to the titration. For Prep-A-Gene this was 0M, 2M, 2.5M, 3M, 3.5M, 4M, 4.5M, and 6M NaClO$_4$. For SFSF, the titration is 0M, 1M, 1.5M, 2M, 2.5M, 3M, 3.5M, and 4M NaClO$_4$.
4. Incubate for 10 minutes, with rocking, at room temperature.
5. Spin and discard supernatant.
6. Wash pellet 2 times with 80% ethanol/50 mM Tris, pH 7.0.
7. Elute DNA in 20μl H$_2$O, 37° C., 10 minutes.
8. Spin and remove supernatant to a separate tube. Repeat elution step and combine supernatants for ~40μl total.
9. Add 2μl, Type II loading dye to each tube.
10. Load onto a 1% agarose, 1×TAE gel. Run for ~25 minutes at 100–130 volts in 1×TAE buffer.
11. Stain with ethidium bromide in H$_2$O (~1: 1000 ) for ~15 minutes. Desrain for ~20-30 minutes.
12. Photograph over UV light with Type 57 Polaroid film. If possible, take negatives with Type 55 film.

Results and Conclusions

Prep-A-Gene shows no elution of DNA until 3M NaClO$_4$, whereas SFSF binds DNA in its native state and elutes strongly at 2.5M NaClO$_4$. Clearly SFSF performs better than Prep-A-Gene.

Example 3

This experiment describes the DNA binding capacity of silicon tetrahydrazide.

Electrophoresis shows that this surface gives good recovery of DNA down to 1M NaClO$_4$ as the binding buffer. This exceeds the Super Fine Super Floss Celite which gives good recovery only down to 2.5M NaClO$_4$. It would also appear from gel electrophoresis analysis that this surface gives equal or greater recovery of DNA down to these lower levels of NaClO$_4$ as the binding buffer, and under native conditions.

Materials

Material of composition described in text (silicon tetrahydrazide)
SUPER FINE SUPER FLOSS (Manville) 1:5 weight:water

Methods

Eight reaction groups are tested. The binding buffer concentrations are 1M, 1.5M, 2M, 2.5M, 3M, 3.5M, 4M with SFSF at 3M NaClO$_4$ as the standard used. See previous experiment.

Results

Silica tetrahydrazide results are analyzed by examination of the agarose gel. There is a large amount of DNA appearing in all lanes and a consistency in the elution pattern.

Conclusion

Silicon tetranhydrazide out-performs SFSF Celite both in the amount of DNA recovered from solution and the concentration of binding buffer required to bring about this recovery. Silicon tetrahydrazide appears from agarose gel electrophorsis analysis to give 100% recovery of DNA from solution even down to 1M NaClO$_4$ as the binding buffer.

Although the invention has been described with respect to specific modifications, the details thereof are not to be construed as limitations, for it will be apparent that various equivalents, changes and modifications may be resorted to without departing from the spirit and scope thereof, and it is understood that such equivalent embodiments are to be included therein.

What is claimed is:

1. A process for purifying DNA which comprises:
   a) providing a silicon tetrahydrazide compound produced by reacting silicon tetrachloride with hydrazine to completion;
   b) binding the DNA to the silicon tetrahydrazide compound; and
   c) recovering the DNA from the silicon tetrahydrazide by eluting in TE buffer, TAE buffer, or TBE buffer or by heating the silicon tetrahydrazide compound with the bound DNA in water.

2. The process of claim 1 wherein the silicon tetrahydrazide is produced by a process comprising:
   a) mixing the hydrazine with tetrahydrofuran and cooling the mixture;
   b) adding the silicon tetrachloride to the hydrazine/tetrahydrofuran mixture and allowing the reaction to occur until production of HCl gas stops, and
   c) ensuring complete reaction of the silicon tetrachloride by adding additional hydrazine to the reaction in (b).

3. The process of claim 1 in which the DNA is recovered by heating the silicon tetrahydrazide compound with the bound DNA in water.

4. The process of claim 1 wherein the DNA is bound to the silicon tetrahydrazide in the presence of less than 2M chaotrope.

5. The process of claim 1 wherein the DNA is bound to the silicon tetrahydrazide compound in the absence of chaotropes.

6. The process of claim 1 wherein the DNA is recovered by heating the silicon tetrahydrazide compound with the bound DNA in water.

* * * * *